US012605200B2

(12) United States Patent
Knopf et al.

(10) Patent No.: US 12,605,200 B2
(45) Date of Patent: Apr. 21, 2026

(54) ELECTROSURGICAL HANDHELD DEVICE AND ALSO A PROXIMAL, CENTRAL AND DISTAL PORTION OF A MAIN BODY OF AN ELECTROSURGICAL HANDHELD DEVICE

(71) Applicant: Olympus Winter & Ibe GmbH, Hamburg (DE)

(72) Inventors: Christoph Knopf, Stockelsdorf (DE); Hannes Miersch, Hamburg (DE); Christian Brockmann, Hollenstedt (DE); Andreas Offt, Reinbek (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 800 days.

(21) Appl. No.: 17/711,373

(22) Filed: Apr. 1, 2022

(65) Prior Publication Data

US 2022/0313348 A1 Oct. 6, 2022

(30) Foreign Application Priority Data

Apr. 1, 2021 (DE) ...................... 10 2021 108 313.3

(51) Int. Cl.
*A61B 18/14* (2006.01)
(52) U.S. Cl.
CPC ................................. *A61B 18/149* (2013.01)
(58) Field of Classification Search
CPC ................................................. A61B 18/149
See application file for complete search history.

(56) References Cited

U.S. PATENT DOCUMENTS

| | | | | |
|---|---|---|---|---|
| 4,149,538 A | * | 4/1979 | Mrava | A61B 18/149 606/46 |
| 5,088,998 A | * | 2/1992 | Sakashita | A61B 18/149 600/105 |
| 5,213,093 A | * | 5/1993 | Swindle | A61B 1/0011 600/920 |
| 5,423,795 A | | 6/1995 | Eckert et al. | |

FOREIGN PATENT DOCUMENTS

| | | |
|---|---|---|
| CN | 111513838 A | 8/2020 |
| DE | 39 17 465 A1 | 3/1990 |

* cited by examiner

*Primary Examiner* — Linda C Dvorak
*Assistant Examiner* — Ryan T Clark
(74) *Attorney, Agent, or Firm* — OLIFF PLC

(57) ABSTRACT

Electrosurgical handheld devices are used mainly for endoscopic applications in urology or in gynaecology. However, the field of use of these instruments is not limited to these regions of the human body and instead also includes the treatment of further organs in the lower part of the human abdomen. The invention makes available an electrosurgical handheld device and also a handle, a main body and an adapter, which are particularly easy and cost-effective to produce and which at the same time ensure a laminar flow of the irrigation liquid at the distal end of the handheld device. This is achieved by the fact that a feedthrough extending through a handle is funnel-shaped, wherein a cross section of the feedthrough tapers from a distal side to a proximal side of the handle.

21 Claims, 3 Drawing Sheets

ELECTROSURGICAL HANDHELD DEVICE AND ALSO A PROXIMAL, CENTRAL AND DISTAL PORTION OF A MAIN BODY OF AN ELECTROSURGICAL HANDHELD DEVICE

The invention relates to a central portion, in particular a handle, for an electrosurgical handheld device, according to the preamble of claim 1. The invention additionally relates to a distal portion, in particular a body, for an electrosurgical handheld device, according to the preamble of claim 8. The invention further relates to a proximal portion, in particular an adapter, for an electrosurgical handheld device, according to the preamble of claim 13. The invention moreover relates to an electrosurgical handheld device according to the preamble of claim 16 and also to an electrosurgical handheld device according to the preamble of claim 17.

Electrosurgical handheld devices, for example resectoscopes, are used mainly for endoscopic applications in urology or in gynaecology, there preferably for treatment in the region of the bladder, the uterus or the prostate. However, the field of use of these instruments is not limited to these regions of the human body and instead also includes the treatment of further organs in the lower part of the human abdomen.

The instruments of the kind described here, for example resectoscopes, have a working element as standard, and an elongate tubular shaft. To treat diseased tissue, this shaft is inserted through an opening into the body of the patient. Various medical instruments for treating and/or examining the patient can be arranged in this shaft tube. For example, an electrode to which radiofrequency alternating current can be applied, and which is positioned at a distal end of an electrode instrument, can be guided through the shaft for radiofrequency surgery. For the manipulation or cutting of tissue, the electrode instrument with the electrode is movable relative to the shaft tube and along a shaft axis, such that, by moving the electrode on or through the tissue, the latter is manipulated.

The electrode instrument is furthermore coupled with its proximal end to the working element. This handling of the working element permits the cutting movement of the electrode. The working element has a movably mounted contact body, which is also designated as a slide. On this contact body, the electrode instrument can be mechanically and releasably coupled to an electrical contact. By way of this mechanical connection, the electrode instrument or the electrode can also be supplied with electrical energy. For this purpose, the contact body has an opening into which an electrical contact of the electrode carrier can be guided for the releasable connection. This opening is designed in such a way that the RF voltage can be applied via an adjoining plug connector. For this purpose, a plug is usually fitted into the socket and is in turn connectable to an RF generator via a line or a cable.

The working element and also the electrode are actuated or longitudinally displaced by an operator. For this purpose, the working element is assigned a grip unit with a handle and a gripping means. To actuate the working element, the operator grasps the handle, and also the gripping means, which is designed as a finger unit or a thumb ring. The handle is fastened to a stationary main body of the working element or to the contact body.

The movement of the working element takes place counter to a spring tension of a spring, which in the working element of the type in question is designed usually as a leaf spring or as a leg spring. One end of this spring is fastened to the contact body or the slide, and the other end is fastened to an end body or an optical guide plate of a strengthening tube. The nature of the springs or the type of actuation of this spring mechanism depends on whether the working element is an active or passive working element. Whereas the spring in the case of an active working element is designed as a compression spring, in the case of a passive working element it is designed as a tension spring. The strengthening tube is fastened to the handle, preferably releasably, via an adapter.

The cutting by the electrode is usually effected by a pulling-back movement of the working element. In the case of the active working element, the electrode is for this purpose pulled back (in the proximal direction) against the spring force of the spring. By contrast, in the case of the passive working element, the electrode is first of all pushed forward (in the distal direction) counter to the spring force, in order then to cut through the tissue during the return movement (in the proximal direction) caused by the relaxation of the spring.

An optical unit can also be guided through the shaft of the instruments described here. Embodiments are known in which the optical unit is guided as a rod lens system or as an optical fibre through the shaft from a proximal end to the distal end. The distal end of the optical unit is directed directly to the surgical region or the site of action of the electrode. At the proximal end of the optical unit, the operator can observe the treatment through an eyepiece or a camera.

The electrode instrument has two parallel electrode arms, which are oriented parallel to the shaft axis. While the two distal ends of the electrode arms carry the electrode, the two proximal ends of the electrode arms can be guided for mechanical and electrical contact into the contact body. For this purpose, the two proximal ends of the electrode arms are guided from the distal direction along the shaft through the main body, the handle and the adapter.

In order to lead the contacting or the proximal ends of the electrode arms away from the optical unit and to create installation space for sealing the various feedthroughs, the tubular electrode arms have an offset. This offset is configured in the manner of an S-bend and forms a step-like shoulder from a distal portion to a proximal portion of the electrode arms. Embodiments are also known in which the two parallel electrode arms are brought together in the proximal direction to form an electrode shaft. The S-bend is then located exactly in the transition region from the two electrode arms to the electrode shaft. For structural reasons, the offset is usually located in a distal region of the electrode instrument. As a result, however, the two offsets or one offset lie in the flow of the irrigation liquid that is flushed from the proximal end of the instrument to the site of treatment. This leads to a massive disruption of the flow, as a result of which the irrigation liquid is unable to form a laminar flow in the viewing field of the optical unit. However, relocation of the S-bend in the proximal direction, for example into the main body, is very complex and is associated with high costs. One reason for this is that the space around the optical unit and, considered in the distal direction, in front of the main body is very limited. Known electrode shafts are therefore designed to be flexible, in order to be deflected into the main body.

Proceeding from this, the problem addressed by the invention is to make available an electrosurgical handheld device and also a handle, a main body and an adapter which are particularly easy and cost-effective to produce and which at the same time ensure a laminar flow of the irrigation liquid at the distal end of the handheld device.

A solution to this problem is described by the features of Claim 1. Accordingly, provision is made that a central portion, in particular handle, of a main body for an electro-surgical handheld device, for example a resectoscope, is releasably connectable, at a distal side, to a distal portion, in particular body, of the main body and, at a proximal side, to a proximal portion, in particular adapter, of the main body. The distal portion, central portion and proximal portion form individual parts of the main body of the working element which can be coupled together in such a way that they form the main body. The distal portion can be designed as a body, the central portion as a handle, and the proximal portion as an adapter, or they can be considered as such in the sense described above.

The central portion has an axial bore through which a shaft-like component of the handheld device, for example the optical unit, can be guided. Parallel to this axial bore, the central portion has at least one feedthrough for passage of an electrode arm of an electrode instrument of the handheld device. This central portion or handle is characterized in that the feedthrough is funnel-shaped, wherein a cross section of the feedthrough tapers from the distal side to the proximal side of the central portion. By virtue of this funnel-shaped configuration of the feedthrough, the at least one electrode arm of the electrode instrument can be guided particularly easily through the feedthrough of the central portion.

Provision is made in particular that a first cross section of the feedthrough at the distal side is oval, and a second cross section of the feedthrough at the proximal side is circular, By virtue of this preferred configuration of the feedthrough of the central portion, the latter is particularly easy to use together with further components of the handheld device.

The invention preferably provides that the first cross section merges continuously into the second cross section of the feedthrough of the central portion, particularly that the oval cross section of the feedthrough merges continuously into the circular cross section of the feedthrough. By means of this continuous transition, i.e. this stepless transition, the end of the electrode arm can be guided particularly easily and on target through the feedthrough of the central portion or handle. Thus, the end of the electrode arm is passed from the side with the larger cross section through the feedthrough to the side with the smaller cross section.

Provision can also be made according to the invention that a main axis of the oval cross section of the feedthrough is oriented vertically, and a secondary axis of the oval first cross section of the feedthrough is oriented horizontally. It is entirely possible here that the axes are also oriented in a different way. However, it has been shown that the here claimed orientation of the axes, particularly in conjunction with the main body of the handheld device, is particularly advantageous. In particular in an illustrative embodiment with two feedthroughs, vertical main axes prove particularly advantageous. In a vertical orientation, the main axes of both feedthroughs are parallel. This orientation permits an offset of both electrode arms in a common spatial direction, and this has a positive bearing on the costs of the electrode instrument.

In a particularly advantageous illustrative embodiment of the invention, provision can be made that the central portion has two feedthroughs for passage of a respective electrode arm of the electrode instrument of the handheld device. Here, both feedthroughs are configured as described above. Both feedthroughs are funnel-shaped and are oriented parallel to each other and also to the axial bore of the central portion.

The here claimed central portion of the main body, or the handle of the handheld device or of the resectoscope, is configured as an injection moulding. Accordingly, this portion is produced from a plastic by means of the known injection moulding technique. This proves particularly advantageous since, in particular, the funnel-shaped configuration of the feedthroughs can be obtained only with great difficulty and cost-intensively when using other production methods and/or with other materials.

A further solution to the aforementioned problem is claimed by a distal portion, in particular a body, of a main body according to claim 8. Accordingly, the distal portion is connected, preferably releasably or permanently, at a distal side to a tubular shaft, in particular by welding, and is releasably connectable, at a proximal side, to a central portion according to claim 1. The distal portion has an axial opening or bore for passage or reception of a shaft-like component of the handheld device. Parallel to this axial opening, the distal portion has at least one feedthrough for passage of an electrode arm of an electrode instrument of the handheld device.

The distal portion, or the body, is characterized in that the at least one feedthrough has an oval or oblong cross section. The electrode arm can be particularly advantageously received by virtue of this oval or oblong configuration of the feedthrough. In particular, if the electrode arm deviates from its tubular or circular cross-sectional shape, and for example has an offset, it can be particularly advantageously inserted movably in the vertically widened feedthrough.

Provision is preferably made that a main axis of the oval cross section of the feedthrough is oriented vertically, and a secondary axis of the oval cross section is oriented horizontally. Thus, the cross section of the feedthrough of the distal portion corresponds substantially to the cross section of the distal side of the feedthrough of the central portion according to claim 1.

In a particularly advantageous illustrative embodiment of the distal portion, provision is made that two feedthroughs for passage of a respective electrode arm of the electrode instrument of the handheld device extend, parallel to each other and also parallel to the axial opening, through the distal portion or body. Both feedthroughs equally have the above-described oval or oblong cross section. This distal portion is configured to receive an electrode instrument with two electrode arms. By virtue of the configuration of the feedthroughs, the two arms of the electrode instrument can be moved to and fro in a very advantageous manner along an axis of the instrument.

Moreover, it is also conceivable that the opening and the at least one feedthrough extending through the distal portion are formed as a common opening, i.e. the respective regions merge into each other, specifically without being separated from each other by a wall.

Claim 13 describes a proximal portion, in particular an adapter, of a main body as a solution to the aforementioned problem. This proximal portion for an electrosurgical handheld device, or a resectoscope, is releasably connectable, at a distal side, to a central portion according to claim 1. At a proximal side, the proximal portion is connected to a tubular shaft. This shaft can be configured, for example, to receive further components of the handheld device, for example an optical unit. This shaft can also be designated as a strengthening tube or optical guide. This adapter also has an axial bore which serves to receive a shaft-like component of the handheld device. Parallel to this axial bore, the proximal portion also has at least one feedthrough for passage of an electrode arm of an electrode instrument. The characterizing feature of the proximal portion is that the at least one feedthrough has a circular cross section. This circular cross section corresponds to the cross section of the proximal side of the feedthrough of the central portion or handle.

A further characterizing feature of the proximal portion can be that the at least one feedthrough has a seal, preferably a fluid seal, which is integrated into the proximal portion or the adapter. During the use of the handheld device, it is conceivable that irrigation liquid passes through the feedthrough. Since the feedthrough is configured to receive an electrical contact of the electrode instrument, it is necessary to avoid the risk of an electrical shortcircuit. In particular, the seal claimed here prevents electrically conductive liquid from passing through the feedthrough of the proximal portion.

It is additionally conceivable that the proximal portion, or the adapter, is characterized by two feedthroughs, wherein both feedthroughs are configured in such a way that they serve to receive a respective electrode arm of the electrode instrument. Both feedthroughs have a circular cross section and are oriented parallel to each other and also to the axial bore. Handling of the proximal portion, and of further components of the handheld device, proves particularly simple and reliable by virtue of this symmetrical setup.

A further solution to the problems formulated above is described by the features of claim 16. Accordingly, an electrosurgical handheld device according to the invention, which can be a resectoscope for example, has an electrode instrument and also a central portion, in particular a handle, of a main body according to claim 1, a distal portion, in particular a body, of the main body according to claim 8, and also a proximal portion, in particular an adapter, of the main body according to claim 12. Thus, the main body is or can be composed of three portions. A distal side of the proximal portion is releasably connectable to a proximal side of the central portion, and a distal side of the central portion is releasably connectable to a proximal side of the distal portion. All of said portions or components of the handheld device have an axial bore and/or an opening. These bores or the opening of the portions or of the components coincide congruently with one another in the connected state and, for example, serve to receive a tubular shaft.

In addition, the distal portion, the central portion and the proximal portion each have at least one feedthrough parallel to the axial bores or to the opening, which feedthroughs likewise merge into one another and serve to receive an electrode arm of an electrode instrument. This handheld device is characterized in that a first cross section of a funnel-shaped feedthrough of the central portion, in particular of the handle, at the distal side of the central portion, is similar, in particular identical, to an oval or oblong cross section of a feedthrough of the distal portion, or of the body. A second cross section of the funnel-shaped feedthrough of the central portion, at the proximal side of the central portion, is identical to a circular cross section of a feedthrough of the proximal portion, or of the adapter. In the connected state of the three portions or components, the feedthroughs of the distal portion, central portion and proximal portion coincide to form an electrode arm guide. Seen from the distal direction, the oval, oblong feedthrough of the distal portion is converted continuously via the central portion into a feedthrough with a circular diameter, wherein this diameter is smaller than the diameter of the feedthrough of the distal portion.

An alternative solution to the problems formulated above is described by the features of claim 17. Accordingly, an electrosurgical handheld device according to the invention, in particular a resectoscope, has an electrode instrument and a main body. This main body in turn has three portions, namely a distal portion, a proximal portion and a central portion. The portions have a common axial bore for receiving an optical unit and, parallel thereto, at least one feedthrough for passage of an electrode arm of the electrode instrument. The at least one feedthrough is composed of three feedthrough portions, wherein a first cross section of a feedthrough portion through the distal portion is oval or oblong, and a third cross section of a feedthrough portion through the proximal portion is circular, and wherein a second cross section of a feedthrough portion through the central portion is funnel-shaped, wherein the funnel-shaped cross section changes continuously from the first cross section to the third cross section. Said three portions together form the one-piece main body.

According to the invention, provision is preferably made that the distal portion, the central portion and the proximal portion have two feedthroughs which are oriented parallel to each other and to the axial bore and serve to receive two electrode arms of the electrode instrument. The individual feedthroughs of said portions or components thus create two parallel electrode arm guides, which are configured to easily receive the proximal ends of the electrode arms. In particular, by virtue of the oblong configuration of the feedthroughs in the distal portion and the funnel-shaped feedthroughs in the central portion or handle, the proximal ends of the electrode arms can particularly advantageously be coupled both mechanically and electrically to the handheld device.

In a further advantageous illustrative embodiment of the invention, provision can be made that the at least one electrode arm of the electrode instrument has an offset. This offset can be configured as a step-like transition between a proximal and a distal region of the electrode arm, wherein the two regions extend parallel to each other. This offset can be configured in particular as an S-bend and serves to guide the proximal end of the electrode arm, configured as an electrical contact, away from the axial bore.

Moreover, a preferred feature of the handheld device is that the at least one feedthrough of the distal portion or the feedthrough portion with the oval or oblong cross section is configured in such a way that the offset of the electrode arm is movable to and fro in the proximal and distal directions in this feedthrough or in the feedthrough portion. The distal regions of the electrode arms are straight, such that the flow behaviour of the irrigation liquid is not disrupted. A laminar flow thus forms in front of the distal end of the handheld device.

Preferably, provision is also made that the second cross section of the at least one funnel-shaped feedthrough of the central portion or of the feedthrough portion at the proximal side of the central portion, and the circular cross section of the at least one feedthrough of the proximal portion, are configured to receive the proximal region of at least one electrode arm. A seal, preferably a fluid seal, can be integrated in this at least one feedthrough of the proximal portion and, in the connected state of the central portion and of the proximal portion, is fixable by the proximal side of the central portion. This seal prevents irrigation liquid from flowing in the proximal direction through the feedthroughs to the electrical contacts of the electrode arms during treatment.

It is further conceivable that the main body with the three portions is configured as n integral metallic body through which the bore and the feedthrough portions extend.

A preferred illustrative embodiment of the invention is explained in more detail below with reference to the drawing, in which.

Figure 1:
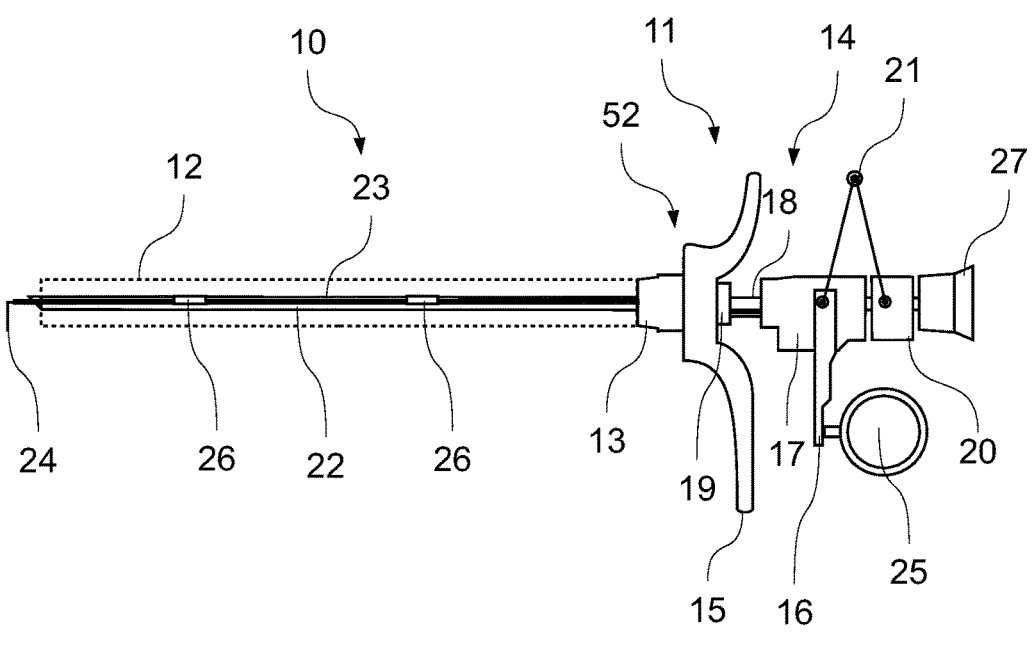
FIG. 1 shows a schematic view of a resectoscope.

A possible illustrative embodiment of an electrosurgical handheld device, namely a resectoscope 10, is depicted highly schematically in FIG. 1. The resectoscope 10 has a working element 11 on which an elongate, tubular shaft 12 can be fastened. This shaft 12 is indicated by hatching in FIG. 1 and is fastened with a proximal end to a main body 52 of the working element 11.

The working element 11 has, in addition to the main body 52, a grip unit 14. This grip unit 14 is assigned to a central portion 15. This portion 15 can have a handle, in particular a releasable handle. While the central portion 15 is arranged fixedly or releasably on the main body 52, a gripping means 16 is assigned to a contact body 17 in the illustrative embodiment of the working element 11 shown here. It is conceivable that the gripping means 16 is screwed firmly on the contact body 17.

The contact body 17 is guided slidingly on a tubular optical guide 18. Since the contact body 17 can move to and fro on the optical guide 18 along a longitudinal direction of the resectoscope 10 or a longitudinal axis of the shaft 12, the contact body 17 is also designated as a slide. While the optical guide 18 is releasably connectable with a distal end to the central portion 15 via a proximal portion 19, in particular an adapter, of the main body 52, an optical guide plate 20 is fastened at a proximal end of the optical guide 18. The tubular optical guide 18 extends through the optical guide plate 20, such that the optical guide 18 is accessible from the proximal direction.

The gripping means 16 and the contact body 17 are connected to the optical guide plate 20 via a spring element 21. This spring element 21 can be a tension spring or a compression spring, depending on the configuration of the working element 11.

Starting from the main body 52 or a distal portion 13, in particular a body, a tubular inner tube 22 extends in the distal direction. An electrode instrument 23 extends parallel to the inner tube 22. This electrode instrument 23 is guided through the distal portion 13, the central portion 15 and the proximal portion 19 or through the three feedthrough portions 49, 50 and 51 and with at least one proximal contact is mechanically and releasably coupled to the contact body 17. The electrode instrument 23 has an electrode 24 at a distal end. An electrical RF voltage can be applied to this electrode 24. The diseased tissue can be manipulated or cut by means of a thermal plasma forming at the electrode 24. For this purpose, the operator moves the gripping means 16, having a thumb ring 25, relative to the central portion 15. For stabilizing the electrode instrument 23, the latter can be guided on the inner tube 22 by guides 26.

For performing the intervention, a rod-like optical unit is guided through the inner tube 22 or through the optical guide 18. A distal end (not visible here) of this optical unit is directed in the direction of the electrode 24, so that the operator has a view of the manipulation of the tissue. This optical unit can be a rod lens system or an optical fibre. As is shown in FIG. 1, an eyepiece 27 or a camera is located at the proximal end of the optical guide.

Figure 2:
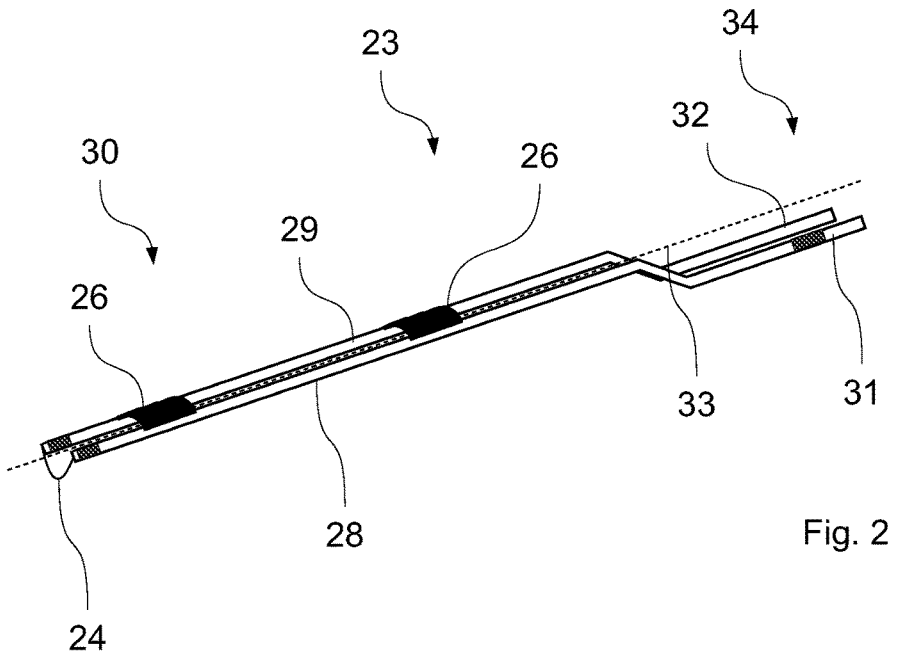
FIG. 2 shows a schematic view of an electrode instrument.

FIG. 2 shows a possible illustrative embodiment of the electrode instrument 23 for the resectoscope 10. This electrode instrument 23 is composed mainly of two electrode arms 28, 29, which are connected to each other at a distal region 30 via the electrode 24. As has been described above, the proximal ends 31, 32 of the two electrode arms 28, 29 serve for both mechanical and electrical coupling to the contact body 17. The two electrode arms 28, 29 are oriented parallel to each other and also to an axis 33. In order to stabilize the two arms 28, 29 and to guide the electrode instrument 23 on the inner tube 22, the electrode arms 28, 29 in the illustrative embodiment shown here are connected to each other via the two guides 26.

The distal regions 30 of the two electrode arms 28, 29 are offset, parallel to each other, in relation to proximal regions 34, in each case by a step-shaped offset 35. This S-shaped offset 35 serves to bring the two proximal ends 31, 32 of the electrode arms 28, 29 into a preferred position for the mechanical and electrical coupling. It has proven particularly advantageous for this offset 35 to be relocated into the proximal region 34, since in this way a particularly good flow behaviour of the irrigation liquid can be established in the distal region 30.

Figure 3:
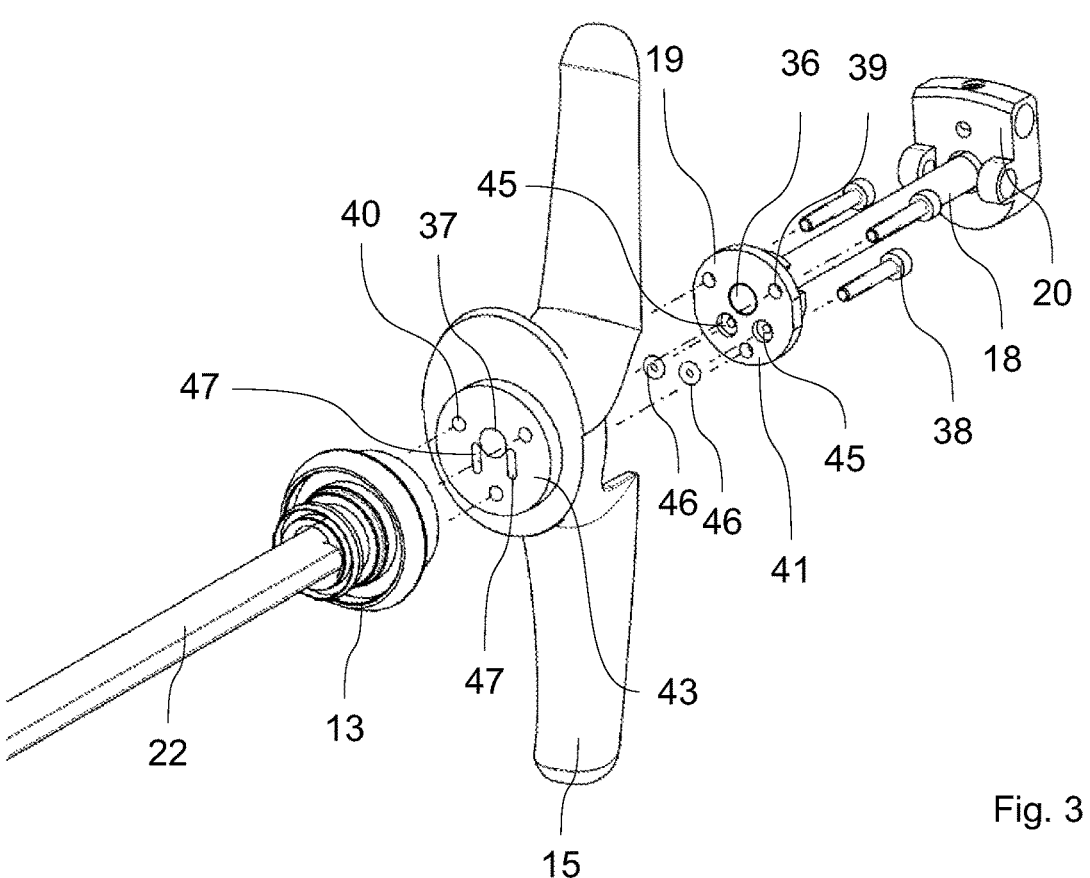
FIG. 3 shows an exploded view of a distal portion, a central portion and a proximal portion.

FIG. 3 shows an exploded view of the distal portion 13, the central portion 15 and the proximal portion 19. In the illustrative embodiment shown here, the proximal portion 19 is connected permanently to the tubular optical guide 18. At the proximal end, this optical guide 18 is connected to the optical guide plate 20. As has been described above, the contact body 17 is pushed over this optical guide 18 in the assembled state of the resectoscope 10. The further features of the optical guide plate 20 will not be discussed in any detail here, since they are not relevant to the claimed invention.

The proximal portion 19, or the adapter, has an axial bore 36 which extends directly into the optical guide 18. Similarly, the central portion 15, or the handle, has an axial bore 37.

The distal portion 13, or the body, also has an axial opening or bore, although this is not visible in FIG. 3. When the distal portion 13, the central portion 15 and the proximal portion 19 are joined together, the axial bores 36, 37 and the opening lie congruently over each other, such that they form a common passage, for example for the optical unit.

The distal portion 13 is assigned the inner tube 22 in the distal direction. This inner tube 22 constitutes a direct continuation of the axial bores 36, 37 and of the optical guide 18.

As is shown in FIG. 3, the distal portion 13, the central portion 15 and the proximal portion 19 are releasably connectable to one another by three screws 38. For this purpose, a distal side 41 of the proximal portion 19 is placed onto a proximal side 42 of the central portion 15, and a distal side 43 of the central portion 15 is placed onto a proximal side 44 of the distal portion 13. The three screws 38 are then guided from the proximal direction through three corresponding bores 39 in the proximal portion 19 and through three corresponding bores 40 (FIG. 4) in the central portion 15 and are screwed into three corresponding bores in the distal portion 13 with an inner thread (not shown here). For repairs or for maintenance purposes, the three portions 13, 15, 19 or the three components can be disassembled again by loosening the screws.

In the state with the portion 13, the portion 15 and the portion 19 joined together, the two proximal ends 31, 32 of the electrode instrument 23 for mechanical and electrical coupling are guided through these three portions 13, 15, 19, in order to then latch in place in the contact body 17. For this purpose, the proximal portion 19 has circular feedthroughs 45. These feedthroughs 45 are spaced apart from each other and arranged parallel to the axial bore 36. To ensure that no irrigation liquid can escape during the use of the resecto-scope 10, these two feedthroughs 45 can each be assigned a sealing ring 46. In the assembled state, these two sealing rings 46 are clamped or locked between the distal side 41 of the proximal portion 19 and the proximal side 42 of the central portion 15.

Figure 4:
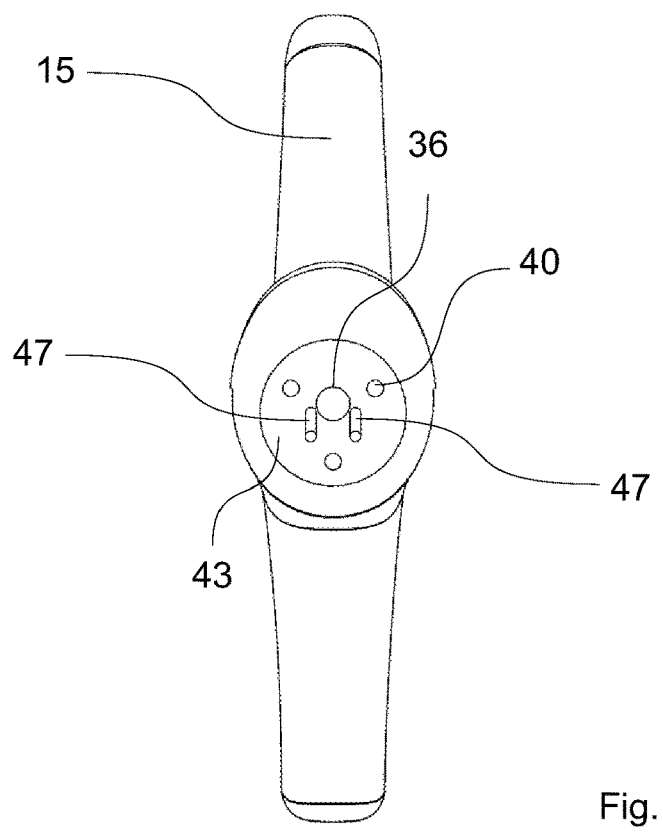
FIG. 4 shows a view of a distal end of the central portion.

The central portion 15 likewise has two parallel feed-throughs 47. These feedthroughs 47 are funnel-shaped, wherein a first cross section of the feedthroughs 47 at the distal side 43 of the central portion 15 is oval or oblong (FIG. 4). A second cross section of the feedthroughs 47 at the proximal side 42 of the central portion 15 has the same cross section or diameter as the feedthroughs 45 of the proximal portion 19. The cross section of the feedthroughs 47 tapers continuously or in a funnel shape from the distal side 43 to the proximal side 42 of the central portion 15 (FIG. 4).

The distal portion 13 also has two feedthroughs 48. These feedthroughs 48 (not visible in FIG. 3) are likewise oriented parallel to each other and also parallel to the bores 37, 36 or to the inner tube 22 and have an oval or oblong cross section matching the cross section of the feedthroughs 47 of the central portion 15 at the distal side 43 of the central portion 15. The feedthroughs 48 of the distal portion 13 do not change in their cross section.

In the assembled state, the feedthroughs 45, 47 and 48 lie congruently over one another, such that they from a con-tinuous guide for the two electrode arms 28, 29. As is shown in the sectional view according to FIG. 5, the electrode instrument 23 is guided through the feedthroughs 45, 47 and 48 in such a way that the offset 35 of the electrode arms 28, 29 lies exactly in the oblong feedthroughs 48 of the distal portion 13.

Figure 5:
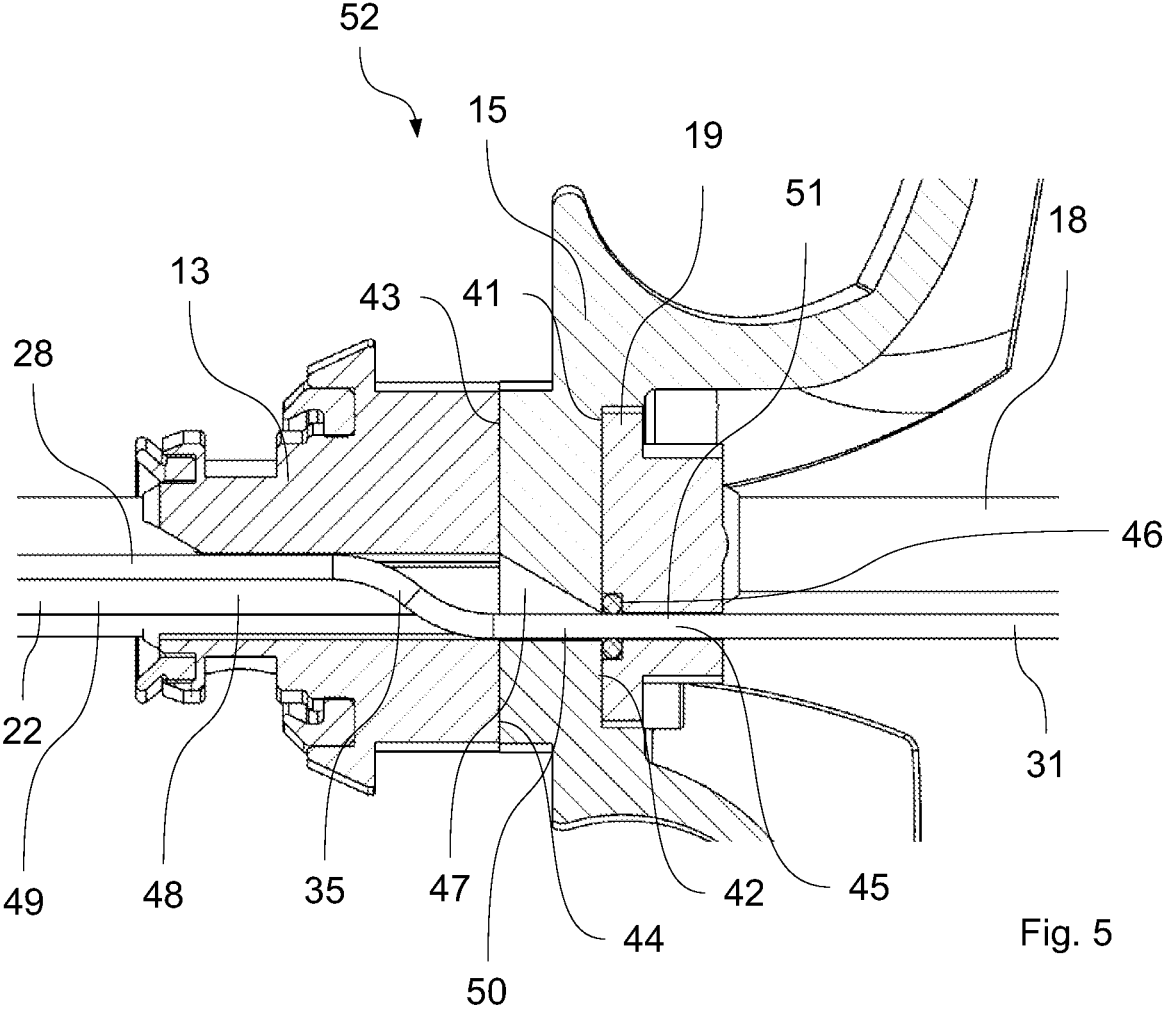
FIG. 5 shows a section through the distal portion, central portion and proximal portion.

It is likewise very clear from FIG. 5 how the funnel-shaped feedthrough 47 of the central portion 15 serves as an insertion aid for the proximal end 31 of the electrode arm 28. Upon insertion of the electrode arm 28 into the feedthrough 48, the end 31 is guided automatically into the feedthrough 45 by the funnel-shaped configuration of the feedthrough 47. Here, the feedthrough 45 is sealed off from the feedthroughs 47, 48 in a fluid-tight manner by the seal 46.

The feedthroughs 48 are configured in such a way that the offset 35 is movable in the distal and proximal directions upon axial displacement of the electrode instrument 23. This is necessary in order, as has been described above, to perform the cutting movement by means of the electrode 24. By relocating the offset 35 into the main body 52, the distal region of the inner tube 22 remains free for undisrupted flow of the irrigation liquid.

Whereas the feedthroughs 45, 48 in the metallic proximal portion 19 and in the metallic main body 52 can be produced by drilling or milling or wire erosion, the more complicated funnel-shaped feedthrough 47 of the central portion 15 can be produced by injection moulding. Accordingly, by means of the presently described configuration of the individual components, production is made easier, costs are reduced, and the flow behaviour of the irrigation liquid is improved.

Alternatively, however, provision is also made that the main body 52 is made in one piece, in which case the main body 52 can be subdivided into the three portions 13, 15, 19. In this illustrative embodiment according to the invention, the axial bores 36, 37 and the feedthrough portions 49, 50, 51 are formed continuously through the entire main body 52.

These integral portions 13, 15, 19 of the main body 52 are all produced from a metal, preferably by drilling, turning, milling and/or erosion, in particular sink erosion.

LIST OF REFERENCE SIGNS

10 resectoscope
11 working element
12 shaft
13 distal portion
14 grip unit
15 central portion
16 gripping means
17 contact body
18 optical guide
19 proximal portion
20 optical guide plate
21 spring element
22 inner shaft
23 electrode instrument
24 electrode
25 thumb ring
26 guide
27 eyepiece
28 electrode arm
29 electrode arm
30 distal region
31 proximal end
32 proximal end
33 axis
34 proximal region
35 offset
36 bore
37 bore
38 screw
39 bore
40 bore
41 distal side
42 proximal side
43 distal side
44 proximal side
45 feedthrough
46 seal
47 feedthrough
48 feedthrough
49 feedthrough portion
50 feedthrough portion
51 feedthrough portion

The invention claimed is:

1. A main body for an electrosurgical handheld device, comprising a handle that is configured to connect at a distal side of the handle to a distal portion of the main body and at a proximal side of the handle to a proximal adapter of the main body, wherein:

the handle has an axial bore for passage of a shaft-like component of the handheld device, and parallel to the axial bore, the handle has at least one feedthrough for passage of an electrode arm of an electrode instrument of the handheld device, the electrode instrument includes at least one electrode arm, the feedthrough is funnel-shaped, cross-sections of the feedthrough gradually taper from the distal side to the proximal side of the handle, such that a first cross-section of the feedthrough at the distal side is oval, and a second cross-section of the feedthrough at the proximal side is circular;

the electrode arm of the electrode instrument has an offset that is configured as a step-like transition between a proximal and a distal region of the electrode arm, and the proximal and the distal region of the electrode arm are oriented parallel to each other; and the offset of the electrode arm of the electrode instrument being provided within the first cross-section that is oval.

2. The main body according to claim 1, wherein the first cross-section of the feedthrough merges continuously into the second cross-section of the feedthrough, the first cross-section of the feedthrough merges continuously into the second cross-section of the feedthrough.

3. The main body according to claim 1, wherein a main axis of the first cross-section of the feedthrough is oriented vertically, and a secondary axis of the first cross-section of the feedthrough is oriented horizontally.

4. The main body according to claim 1, wherein the electrode instrument comprises two electrode arms and the handle comprises two feedthroughs for passage of a respective electrode arm of the electrode instrument of the handheld device, and both feedthroughs are funnel-shaped and are oriented parallel to each other and also to the axial bore.

5. The main body according to claim 4, wherein the main axis of the first cross-section of each feedthrough are oriented parallel to each other.

6. The main body according to claim 1, wherein the portion is produced as an injection moulding made of plastic.

7. The main body according to claim 1, wherein the distal body portion has at least one feedthrough with an oval or oblong cross-section that corresponds to a distal cross-section of the at least one feedthrough of the handle.

8. The main body according to claim 7, wherein a main axis of the first cross-section of the feedthrough of the distal body portion is oriented vertically, and a secondary axis of the first cross-section is oriented horizontally.

9. The main body according to claim 7, wherein the electrode instrument includes two electrode arms, and the distal body portion includes two feedthroughs for passage of a respective electrode arm of the electrode instrument of the handheld device, wherein both feedthroughs have an oval or oblong cross-section and are oriented parallel to each other and an axial opening.

10. The main body according to claim 9, wherein the main axis of the first cross-section of each feedthrough of the distal body portion are oriented parallel to each other.

11. The main body according to claim 7, wherein an opening and the at least one feedthrough of the distal body portion are formed as a common opening.

12. The main body according to claim 1 wherein the adapter has at least one feedthrough with a circular cross-section that corresponds to a proximal cross-section of the at least one feedthrough of the handle.

13. The main body according to claim 12, wherein the at least one feedthrough of the adapter has a seal, which is integrated into the adapter.

14. The main body according to claim 12, wherein the electrode instrument includes two electrode arms and the adapter includes two feedthroughs for passage of a respective electrode arm of the electrode instrument of the handheld device, wherein both feedthroughs have a circular cross-section and are oriented parallel to each other and also to the axial bore.

15. The electrosurgical handheld device comprising the electrode instrument and the main body according to claim 1, wherein a first cross-section of a funnel-shaped feedthrough of the handle, at the distal side of the handle is identical to an oval or oblong cross-section of a feedthrough of the distal body portion, and a second cross-section of the funnel-shaped feedthrough of the handle at the proximal side of the handle is identical to a circular cross-section of a feedthrough of the adapter, wherein, in a connected state, the feedthroughs of the distal body portion, handle and adapter coincide to form an electrode arm guide.

16. The electrosurgical handheld device according to claim 15, wherein the at least one feedthrough of the distal body portion or a feedthrough portion with the oval or oblong cross-section is configured in such a way that an offset of the electrode arm is movable along proximal and distal directions in this feedthrough or in the feedthrough portion.

17. The electrosurgical handheld device according to claim 15, wherein the second cross-section that includes at least one funnel-shaped feedthrough or of a feedthrough portion at the proximal side of the handle, and the circular cross-section of the at least one feedthrough or of the feedthrough portion of the adapter, are configured to receive a proximal region of at least one electrode arm.

18. The electrosurgical handheld device according to claim 15, wherein a seal is integrated into the at least one feedthrough of the adapter and, in the connected state of the handle and of the distal body portion, is fixable by the proximal side of the handle.

19. The electrosurgical handheld device according to claim 15, wherein the main body is configured as an integral metallic body through which the bore and the feedthrough extend.

20. The electrosurgical handheld device comprising the electrode instrument and the main body according to claim 1, wherein a first cross-section of the feedthrough at the distal body portion is oval or oblong, and a third cross-section of the feedthrough at the adapter is circular, and wherein a second cross-section of the feedthrough at the handle is funnel-shaped, wherein the second cross-section changes continuously from the first cross-section to the third cross-section.

21. The electrosurgical handheld device according to claim 20, wherein the electrode instrument includes two electrode arms and the distal body portion, the handle and the adapter each have two feedthroughs which are oriented parallel to each other and to the axial bores and/or an opening and serve to receive the two electrode arms of the electrode instrument.

* * * * *